United States Patent [19]

McGinn et al.

[11] Patent Number: 4,888,547

[45] Date of Patent: Dec. 19, 1989

[54] METER USING A MICROWAVE BRIDGE DETECTOR FOR MEASURING FLUID MIXTURES

[75] Inventors: Vincent P. McGinn, Tulsa, Okla.; Ira B. Goldberg, Thousand Oaks, Calif.

[73] Assignee: Rockwell International Corporation, El Segundo, Calif.

[21] Appl. No.: 299,695

[22] Filed: Jan. 23, 1989

[51] Int. Cl.[4] ............................................ G01N 22/00
[52] U.S. Cl. ........................... 324/58.5 A; 324/58.5 R; 324/58.5 B; 73/61.1 R
[58] Field of Search ...................... 324/58.5 A, 58.5 B, 324/58.5 R, 58 A, 58 B, 55 R; 73/61.1 R, 61 R; 333/248

[56] References Cited

U.S. PATENT DOCUMENTS

| | | | |
|---|---|---|---|
| 2,982,855 | 5/1961 | Wickersham | 250/83.1 |
| 3,103,627 | 9/1963 | Schneider | 324/58.5 |
| 3,498,112 | 3/1970 | Howard | 324/58.5 A |
| 3,956,695 | 5/1976 | Stamm | 324/58.5 A |
| 4,423,623 | 1/1984 | Ho et al. | 73/61 R |

FOREIGN PATENT DOCUMENTS 0268399 5/1988 European Pat. Off. ....... 324/58.5 A
607133 5/1978 U.S.S.R. .

Primary Examiner—Reinhard J. Eisenzopf
Assistant Examiner—Jack B. Harvey
Attorney, Agent, or Firm—Craig O. Malin; John C. McFarren; H. Fredrick Hamann

[57] ABSTRACT

A meter measures the flow rate of a mixture by measuring a frequency characteristic of microwave propagation within a waveguide which forms a part of the conduit through which the mixture flows. Spaced apart slots in the waveguide form transmitting and detecting antennas which are connected to the output ports of a microwave bridge. An oscillator generates microwaves which are fed to the input of the microwave bridge. The output of the bridge is the difference in power transmitted through the two antennas. This signal is fed to a phase sensitive detection system and the output can be correlated to the flow rate of the mixture. In one embodiment, a computer control unit and computer controlled switches are provided to switch the microwave bridge in and out of the circuit so that both the flow rate and the concentration of an ingredient can be measured.

10 Claims, 2 Drawing Sheets

METER USING A MICROWAVE BRIDGE DETECTOR FOR MEASURING FLUID MIXTURES

BACKGROUND OF THE INVENTION

This invention relates to the field of meters and particularly to meters for measuring the concentration and flow rate of fluid mixtures.

In order to control processes which utilize fluid mixtures of two materials, continuous or rapid monitoring of the concentration of the mixture and its flow rate is highly desirable. Examples of such processes include the disposal of sewage, the manufacture of paper from paper pulp, and coal water slurry transport systems for use in energy applications.

Because of the nature of many mixtures, most conventional measurement techniques are not completely satisfactory. The erosive nature of the flowing media precludes the use of devices which have moving parts or fragile components which must be immersed in the flow. Instruments which require pressure transmission through fine openings or flow through small by-pass tubes have problems with clogging caused by solid particles in the mixture.

A meter which attempts to overcome these problems is described in U.S. Pat. No. 4,423,623 by William W. Ho, Alan B. Harker, Ira B. Goldberg (also a co-inventor of the present invention), and Kwant E. Chung. This prior patent (which is hereby incorporated into the present patent by reference) utilizes microwaves to determine the concentration and velocity of the fluid mixture. The prior art meter uses a waveguide which contains the flowing mixture. Two pair of probes extend through the wall of the waveguide into the mixture to transmit and detect microwaves in the mixture. A lock-in amplifier is coupled to the probes to determine a frequency characteristic of the microwaves propagating within the waveguide section. The frequency characteristic is related to the concentration of the mixture.

SUMMARY OF THE INVENTION

It is an object of the invention to provide a meter for measuring the composition and velocity of a fluid mixture whch does not have probes extending into the mixture.

It is an object of the invention to provide a meter for measuring the composition and velocity of a fluid mixture which utilizes only a single pair of antennas to propagate and to detect microwaves in a waveguide containing the flowing mixture.

According to the invention, a waveguide forms a part of the conduit through which a mixture flows. Microwaves are transmitted into the waveguide through a slot in the wall of the waveguide which forms a transmitting antenna for a microwave generator. The slot is filled with an insulator and can be blended into the wall of the waveguide without projecting into the flowing mixture. A similar slot is formed at a predetermined distance downstream from the first slot to form a detecting antenna for detecting microwaves which travel through the mixture in the waveguide.

The transmitting and detecting antennas are connected to the output ports of a microwave bridge such as a circular or hybrid-T. A microwave generator, such as a voltage controlled oscillator, is connected to the input port of the microwave bridge. A characteristic of a microwave bridge is that it divides the input microwave energy equally between its two antenna ports. Another characteristic of the microwave birdge is that its output is the difference in the power which is actually transmitted through the two antenna ports. Inherent differences in the concentration of the ingredients flowing through the waveguide will cause impedance differences at the two locations of the antennas. This will cause different impedances at the transmitting and at the detecting antennas which cause a difference in the power transmitted by the two antennas as measured at the output port of the microwave bridge.

The output of the microwave bridge is connected to a phase sensitive detection system which uses this signal to provide a frequency characteristic of microwave propagation. The flow rate of the mixture can be calculated using an autocorrelation function to determine the time for the mixture to travel the predetermined distance between the two antennas.

In a preferred embodiment, a computer control unit and computer controlled switches are provided to switch the microwave bridge into and out of the circuit. When the microwave bridge is switched into the circuit, the flow rate is measured as described above using the computer to provide the autocorrelation calculation. When the microwave bridge is switched out of the circuit, the microwave generator and the detecting system are connected directly to their respective antennas and the concentration of an ingredient is measured as described in U.S. Pat. No. 4,423,623.

These and other objects and features of the invention will be apparent from the following detailed description taken with reference to the accompanying drawings.

DESCRIPTION OF THE INVENTION

The flowmeter of the present invention is an improvement over the flowmeter described in U.S. Pat. No. 4,423,623 (incorporated herein by reference) in that it can measure both the concentration and flow rate of a flow mixture using only a single pair of microwave antennas rather than two pair of antennas. Additionally, the antennas in the present flowmeter are confined to the wall thickness of the waveguide and do not extend into the mixture being measured. Both these flowmeters transmit and detect microwaves that propagate down a waveguide which is a segment of the conduit through which the mixture being measured flows. The electronic circuit of the flowmeter determines a frequency characteristic of the microwave as it propagates down the waveguide and relates this characteristic to the composition of the mixture.

Figure 1:
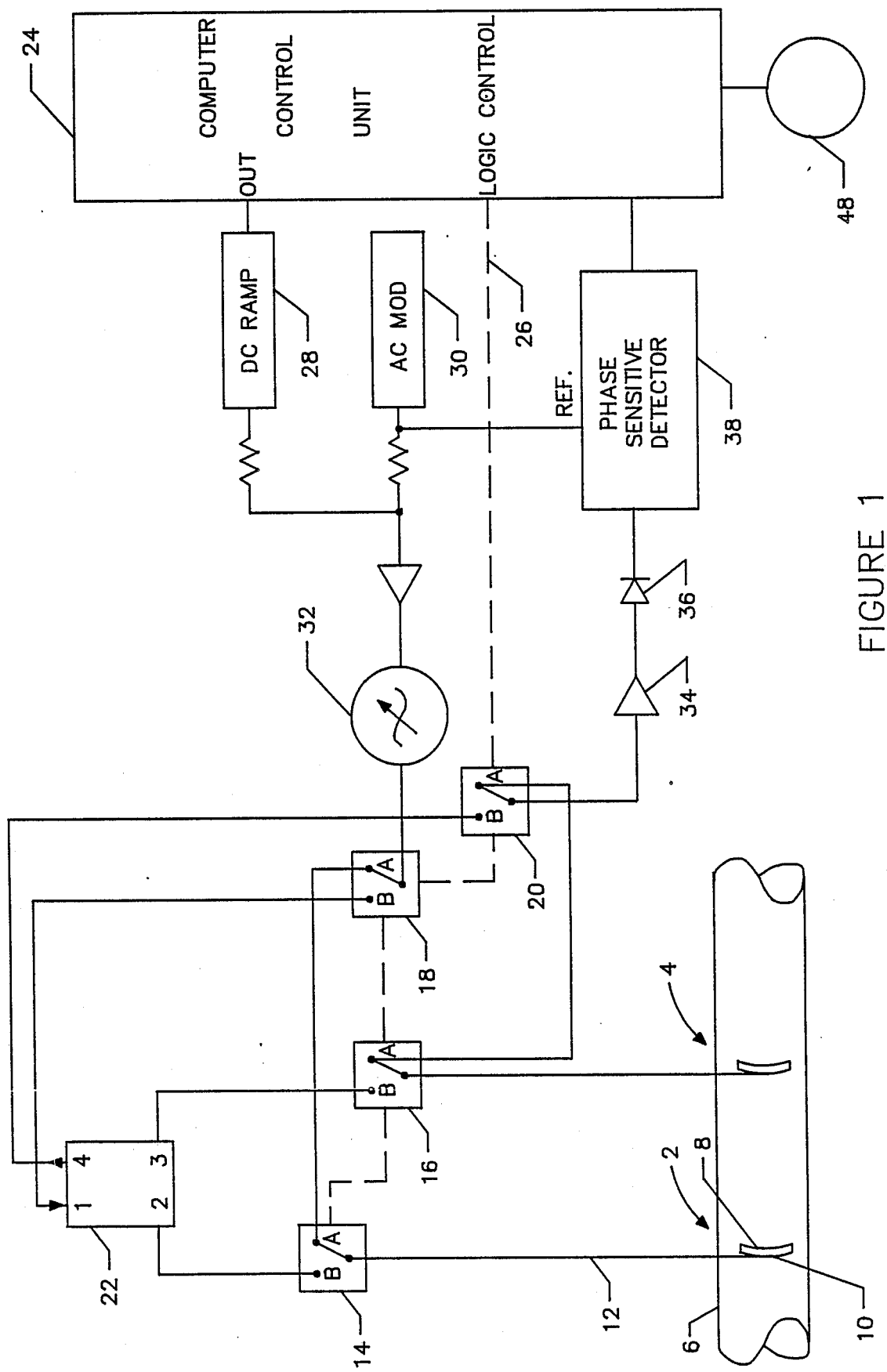
FIG. 1 is a block diagram of the flowmeter.

FIG. 1 is a block diagram showing the microwave antennas 2,4 in waveguide 6. The antenna 2 consists of a slot or opening 8 cut through the wall of waveguide 6. Opening 8 is filled with an insulating material 10 which can be configured to provide a continuous interior surface allowing smooth leak-free flow. The center of coaxial cable 12 is attached to the edge of slot 8 to provide a coupling of the microwave energy between the wave guide and the circuit. The coupling is expected to exceed 50%. Good coupling increases the sensitivity of the flowmeter, particularly if lossy or absorptive fluids are being measured. According to actual measurements, recessed coupling loops used in the prior art lost more than 99.9% of the power because of poor coupling between the cable and pipe waveguide.

Either longitudinal slots (parallel to the flow) or lateral slots (traverses to the flow) can be cut in the waveguide depending on whether TE mode (for longitudinal slots) or TM mode (for lateral slots) of microwave propagation are to be launched into the pipe. Optimum dimensions of the slots are determined empirically.

Four computer operated switches are shown in FIG. 1: power input switch 14, power output switch 16, bridge input switch 18, and bridge output switch 20. When all the switches are in position "A", microwave bridge 22 is removed from the circuit and the concentration of the mixture in the waveguide is measured. When the switches are set to position "B", microwave bridge 22 is included in the circuit and the flow rate of the mixture is measured. The operation of these switches can be controlled by a logic control unit in a computer control unit 24 as shown by dashed control lines 26. The switches can also be controlled by an automatic control unit, or even by manual control.

Concentration (switch position "A") is measured as described in U.S. Pat. No. 4,423,623. In the example shown in FIG. 1, computer 24 is used to apply DC signal 28 on which is superimposed a small AC signal 30 to create frequency modulation (i.e. 10 KHz to 1 MHz) superimposed on a repetitive (1 to 100 Hz) sawtooth microwave signal of slowly increasing frequency. A stable analog, phase locked loop, or synthesized voltage controlled oscillator 32 can be used as the source of microwaves. The input power enters transmitting antenna 2. The power from pipe waveguide 6 exits through detecting antenna 4 and is directed through a microwave amplifier 34, detector 36, and phase sensitive detection system 38.

Figure 2:
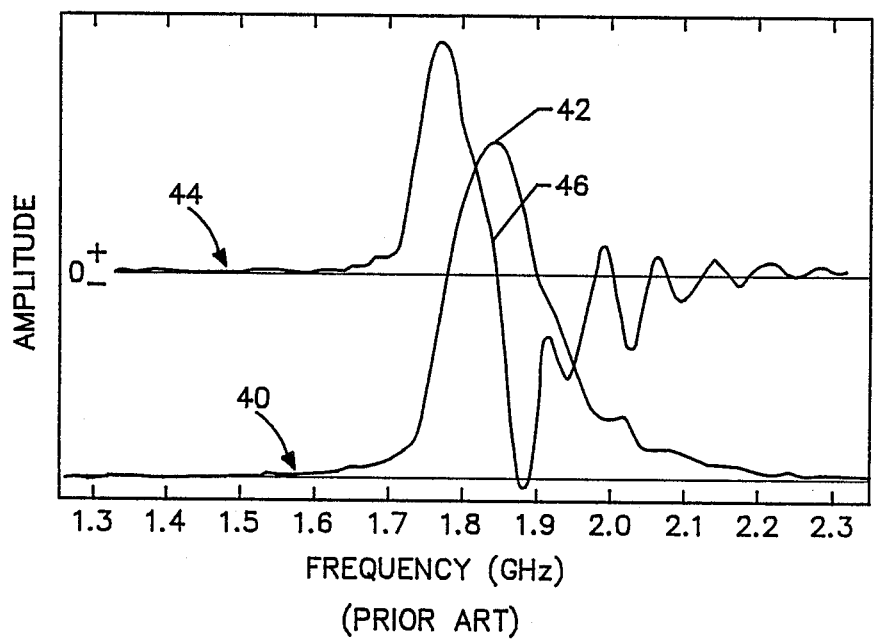
FIG. 2 are curves taken from U.S. Pat. No. 4,423,623 showing the DC output signal of the flowmeter and the phase sensitive component of the signal.

Curve 40 in FIG. 2 is the direct output, DC component of the signal received by detecting antenna 4 when transmitting antenna 2 is swept at frequencies from 1.3 to 2.3 GHz with the waveguide filled with a mixture of acetone and water. The maximum signal 42 corresponds to a frequency slightly above the cut-off frequently of the lowest frequency mode of microwave propagation in the wave guide. This corresponds to the $TE_{11}$ mode for circular waveguide 6.

The phase senstive output of the frequency modulated signal is shown in curve 44 and it is the derivative of curve 40. Maximum signal 42 corresponds to zero crossing 46. When zero crossing 46 is reached, the frequency or voltage to voltage controlled oscillator 32 is monitored. This value is used to determine the concentration of the mixture in a manner similar to the procedure described in U.S. Pat. No. 4,423,623.

In order to measure flow rate, switches 14, 16, 18, and 20 are set in the "B" position. This brings microwave bridge 22 (such as a hybrid-T, a magic-T, or a circulator) into the circuit. Power entering bridge 22 at port 1 is equally divided between ports 2 and 3, each leading to an antenna. The difference in the power transmitted through the antennas is measured at port 4. The microwave bridge 22 functions much like a Wheatstone bridge of which it is the microwave analog.

Microwave bridge 22 is used to sense an imbalance caused by impedance differences between the two slot antennas. The impedance difference is caused by a difference in the concentrations of the components of the mixture in different regions of the waveguide. The concentration difference, in turn, causes a difference in the dielectric constant and hence a difference in impedance at the antenna.

Figure 3A:
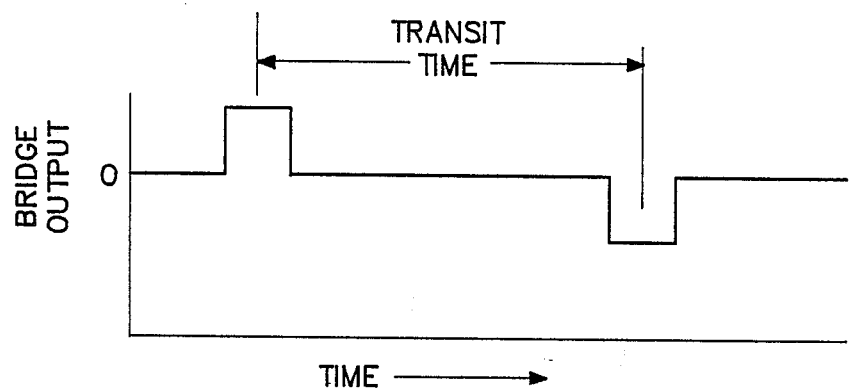
FIGS. 3A and 3B are an illustration of the correlation function used to determine the transit time of the mixture flowing from one antenna to the other.

Because the bridge output at port 4 is a measure of the concentration difference between the two antennas, it can be used with a correlation function to determine the transit time of the fluid from the upstream antenna to the downstream antenna. When operating in the velocity measurement regime, the source power is set to maximum frequency 42 (FIG. 2). Frequency modulation is continued to enhance sensitivity. Assuming that a segment of mixture containing a different composition than the other regions in the pipe waveguide flows past either antenna in succession, then a bridge signal such as shown in FIG. 3A is obtained as a function of time. The nature of the bridge is such that an equal magnitude but opposite phase signal will be obtained when the different segment moves from the upstream antenna to the downstream antenna.

Figure 3B:
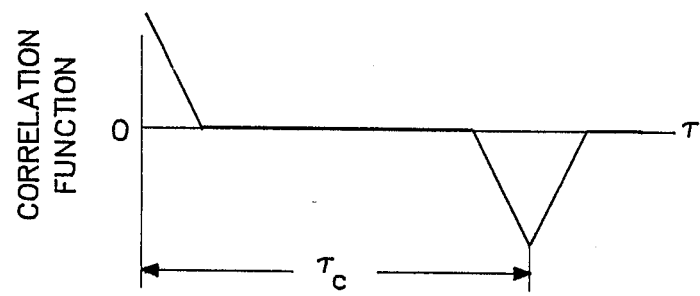

The autocorrelation function, C, is defined as follows:

$$C = \int_0^\infty S(t)S(t + \tau)dt,$$

where S is the bridge output, $\tau$ is the correlation variable and t is the time. The autocorrelation function is plotted in FIG. 3B.

The correlation time $\tau_c$ occurs when a negative maxium correlation function is obtained. This is linearly related to the time for the different segment in the mixture to move from the upstream antenna to the downstream antenna. This function and relationship together with the relationships for concentration can be programmed in computer control unit 24 to provide a suitable display 48 of the concentration and flow rate.

The preferred embodiments of this invention have been illustrated by the examples described above. Modifications and additional embodiments, however, will undoubtedly be apparent to those skilled in the art. For example, the four computer operated switches 14, 16, 18, and 20 shown in FIG. 1 could be manually operated switches. Furthermore, equivalent elements may be substituted for those illustrated and described herein, and certain features of the invention may be utilized independently of other features. Consequently, the exemplary embodiments should be considered illustrative, rather than inclusive, while the appended claims are more indicative of the full scope of the invention.

What is claimed is:

1. A meter comprising:
    a waveguide through which a substance to be measured can flow;
    a transmitting antenna in the waveguide;
    a detecting antenna in the waveguide spaced a predetermined distance from the transmitting antenna along the flow path of the waveguide;
    a microwave bridge having a power input port, a transmitting output port connected to the transmitting antenna, a detecting output port connected to the detecting antenna, and a bridge output port which measures the difference in the power to the two antennas;

a microwave generator connected to the input of the microwave bridge;

a phase sensitive detection system connected to the bridge output port for providing an output of a frequency characteristic of microwave propagation within the waveguide; and a switch connected to each of the ports of the microwave bridge for switching the microwave bridge out of the circuit and connecting the transmitting antenna to the microwave generator and the detecting antenna to the phase sensitive detection system.

2. The meter as claimed in claim 1 including a display connected to the output of the phase sensitive detection system for displaying the frequency characteristic of microwave propagation within the waveguide.

3. The meter as claimed in claim 1 wherein the phase sensitive detection system comprises:

an amplifier connected to the bridge output port;
a diode detector connected to the amplifier for rectifying signals; and
a lock-in amplifier connected to the detector.

4. The meter as claimed in claim 1 including a computer control unit having a ramp signal output connected to the microwave generator, an input connected to the output of the phase sensitive detection system, and a meter output which provides a signal related to a frequency characteristic of microwave propagation within the waveguide.

5. The meter as claimed in claim 4 wherein:

the microwave generator comprises a voltage controlled oscillator, an amplifier, a source of DC ramp voltage, and a source of an AC modulation signal;

the ramp signal output of the computer control unit is connected to the source of DC ramp voltage, the output of the DC ramp voltage is connected to the amplifier, the output of the amplifier is connected to the voltage controlled oscillator, and the output of the voltage controlled oscillator is connected to the microwave bridge power input port; and wherein the source of an AC modulation signal is connected to the amplifier and to the phase sensitive detector to provide a reference to the phase sensitive detector and to superimpose a small AC signal modulation on the ramped output of the microwave generator.

6. The meter as claimed in claim 1 wherein the transmitting and receiving antennas comprise slots cut into the wall of the waveguide and filled with insulating material.

7. The meter as claimed in claim 6 wherein the slots are cut parallel to the direction of flow in the waveguide.

8. The meter as claimed in claim 6 wherein the slots are cut transverse to the direction of flow in the waveguide.

9. The meter as claimed in claim 1 including a computer and a logic control network connected to the switch to control operation of the switch.

10. A meter for measuring an ingredient in a mixture of ingredients and for measuring the flow rate of the mixture, comprising:

a waveguide through which a mixture can flow;
a transmitting slot antenna in the waveguide:
a detecting slot antenna in the waveguide spaced a predetermined distance from the transmitting slot antenna along the flow path of the waveguide;
a first switch connected to the transmitting slot antenna;
a second switch connected to the detecting slot antenna;
a microwave bridge having a transmitting output port connected to the first switch, a detecting output port connected to the second switch, a bridge output port which measures the difference in the power to the two antennas, and a power input port;
a third switch connected to the power input port of the microwave bridge;
a fourth switch connected to the bridge output port of the microwave bridge;
a microwave generator connected to the third switch;
a phase sensitive detection system capable of determining a frequency characteristic of microwave propagation within the waveguide connected to the fourth switch;
a computer control unit having a ramp signal output connected to the microwave generator, a detection signal input connected to the phase sensitive detection system, a logic control output connected to the four switches, an internal memory relating the frequency characteristic to the concentration of an ingredient in the mixture, a correlator for measuring flow rate based upon the bridge output, and a meter output; and
a display connected to the computer control meter output for displaying the measured ingredient concentration and mixture flow rate.

* * * * *